US00PP28883P2

(12) United States Plant Patent
Egger

(10) Patent No.: US PP28,883 P2
(45) Date of Patent: Jan. 16, 2018

(54) ×*HEUCHERELLA* PLANT NAMED 'PLUM CASCADE'

(50) Latin Name: ×*Heucherella* hybrid
Varietal Denomination: Plum Cascade

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 14/999,759

(22) Filed: Jun. 22, 2016

(51) Int. Cl.
*A01H 5/12* (2006.01)
*A01H 5/02* (2006.01)

(52) U.S. Cl.
USPC ..... Plt./441
CPC ..... *A01H 5/02* (2013.01); *A01H 5/12* (2013.01)

(58) Field of Classification Search
USPC ..... Plt./441, 486, 440
CPC ..... A01H 5/012; A01H 5/02; A01H 5/00; A01H 5/12
See application file for complete search history.

(56) References Cited

PUBLICATIONS

Terra Nova Nurseries *Heucherella* 'Plum Cascade' retrieved on Jul. 26, 2017, retrieved from the Internet at <http://www.terranovanurseries.com/gardeners/heucherellaplumcascade-p-842.html> one page.*

Garden Center 2016 Terra Nova Nurseries displays new varieties at 2016 California Spring Trials, retrieved on Sep. 11, 2017, retrieved from the Internet at http://www.gardencentermag.com/article/terra-nova-2016-trials/ 2 pp. (Year: 2016).*

* cited by examiner

*Primary Examiner* — June Hwu
(74) *Attorney, Agent, or Firm* — Klarquist Sparkman, LLP

(57) ABSTRACT

A new and distinct ×*Heucherella* plant substantially as shown and described, characterized by a trailing habit, a strongly lobed leaf, leaves than are purple silver in color, light pink flowers, and excellent vigor.

1 Drawing Sheet

Botanical denomination: ×*Heucherella* hybrid.
Variety designation: 'Plum Cascade'.

BACKGROUND OF THE INVENTION

The present invention relates to a new and distinct cultivar of ×*Heucherella* and given the cultivar name of 'Plum Cascade'. ×*Heucherella* is in the family Saxifragaceae. ×*Heucherella* 'Plum Cascade' originated from a controlled cross between a proprietary unreleased, unpatented seedlings *Heuchera* 'K865-5', as the seed parent, and *Tiarella* '143-12', as the pollen parent.

Compared to the seed parent *Heuchera* 'K865-5', the new cultivar is trailing rather than clumping and leaves that are cut uncut and more silver than purple.

Compared to the pollen parent, *Tiarella* '143-12', the new cultivar has silver purple leaves rather than green.

Compared to ×*Heucherella* 'Twilight', U.S. Plant Pat. No. 25,723, the new cultivar is trailing rather than clumping and with a lobed leaf rather than not lobed.

SUMMARY OF THE INVENTION

The following traits have been repeatedly observed and are determined to be the unique characteristics of 'Plum Cascade'. This new ×*Heucherella* is unique in having the following characteristics:

1. a trailing habit,
2. a strongly lobed leaf, 3. leaves than are purple silver in color,
4. light pink flowers, and
5. excellent vigor.

This new cultivar has been reproduced only by asexual propagation (cuttings and tissue culture). Each of the progeny exhibits identical characteristics to the original plant. Asexual propagation in 2013 by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of an eight-month-old ×*Heucherella* 'Plum Cascade' grown outdoors in the shade in a one gallon container in May in Canby, Oreg.

FIG. 2 shows a photo of one-year-old plants in the garden in part shade in early November in Canby, Oreg.

DETAILED PLANT DESCRIPTION

The following is a detailed description of the new ×*Heucherella* cultivar based on observations of eight-month-old specimens in August growing in one gallon containers outside in the shade in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart,* $5^{th}$ edition, 2007.

Plant:

*Form*.—Basal rosette and trailing, herbaceous perennial.

*Hardiness*.—USDA Zone 4 to 9.

*Size*.—16 cm tall from top of the foliage to the soil and 64 cm wide.

*Habit*.—Mounding and trailing.

*Vigor*.—Excellent.

*Roots*.—Fibrous, freely branching, fine, and white in color.

Stem:

*Size*.—Grows to 5 mm wide and 35 cm long.

*Internode length*.—0.5 mm to 6 mm.

*Stem color*.—Grey Brown 199B near base blending to Greyed Purple 187A near tips.

Leaf:

*Type*.—Simple.

*Arrangement*.—Rosette and alternate.

*Shape*.—Broadly ovate.

*Blade size*.—Grows to 10 cm long and 9.5 cm wide.

*Lobing/division*.—7 palmate main lobes with shallower secondary lobes, the terminal the longest.

*Venation*.—Palmate, topside Greyed Purple N186B, bottom side closest to Purple N77A.

*Margins*.—Crenate, undulation absent to weak.

*Apex*.—Mucronulate.

*Base*.—Cordate.

*Surface texture*.—Glandular hairs on both sides.

*Petiole description*.—Grows to 11 cm long on stem leaves and 14 cm long on rosette leaves and 2 mm wide, glandular hairs, Grey Brown 199B.

*Leaf color*.—Spring topside Grey 201B tinted Purple 79A with the veins N186B, bottom side Purple N77A; summer topside Grey 201B tinted Purple 79A with the veins N186B later lightening to Grey 201B, bottom side Purple N77A; fall and winter leaves topside closest to Purple N77C with dark veins Greyed Purple N186B, bottom side closest to Greyed Purple 187A.

Inflorescence:

*Size*.—Grows to 2.5 cm wide and 12 cm long.

*Type*.—Raceme.

*Attitude*.—Upright to semi-upright.

*Number of flowers per raceme*.—About 100.

*Density of flowers*.—Medium.

*Number of racemes*.—About 17.

*Peduncle*.—Grows to 17 cm tall, 2 mm wide at base, Greyed Purple 187A, glandular hairs, sometimes with one to two side branches and 0 to two leaves (blades grow to 3 cm long and 2.5 cm wide, ovate, coarsely serrate, tip acute, base cordate, glandular hairs on both sides, topside Grey 201B tinted Purple 79A with the veins N186B, bottom side Purple N77A).

*Pedicel*.—Grows to 1 mm long, with glandular hairs, Greyed Purple 187A.

*Bloom period*.—May to September with sporadic rebloom through November, in Canby, Oreg.

Flower bud:

*Size*.—1.5 mm wide and 3 mm long.

*Description*.—Glandular puberulent, ovoid.

*Color*.—Red Purple 65A.

Flower:

*Type*.—Perfect.

*Shape*.—Campanulate.

*Size*.—5 mm deep and 4 mm wide.

*Attitude*.—Outward to down-facing.

*Petal description*.—5 in number, linear, 3 mm long, tip acuminate, base attenuate, margin entire, glabrous on top and bottom, Red Purple 62D on both sides.

*Calyx description*.—4 mm deep and 4 mm wide, with 5 lobes, divided ½ way to the base, campanulate, glandular hairs on both sides, tip acute, margin entire, both sides Purple 79C (Red Purple 72D at base).

*Stamen description*.—10 in number, filaments 3 mm long, White NN155C, anthers less than 1 mm, Greyed Orange N170A, pollen none.

*Pistil description*.—One central two beaked pistil, 6 mm long, White NN155C tinted Purple 72B.

*Fragrance*.—None.

*Lastingness*.—Each raceme blooms for about 3 weeks on the plant.

Fruit and seed: None.

Disease and pest tolerance: The new cultivar is typical to the genus. No known resistances to pests or diseases. No problems have been found in Canby, Oreg.

I claim:

1. A new and distinct ×*Heucherella* plant as herein illustrated and described.

* * * * *

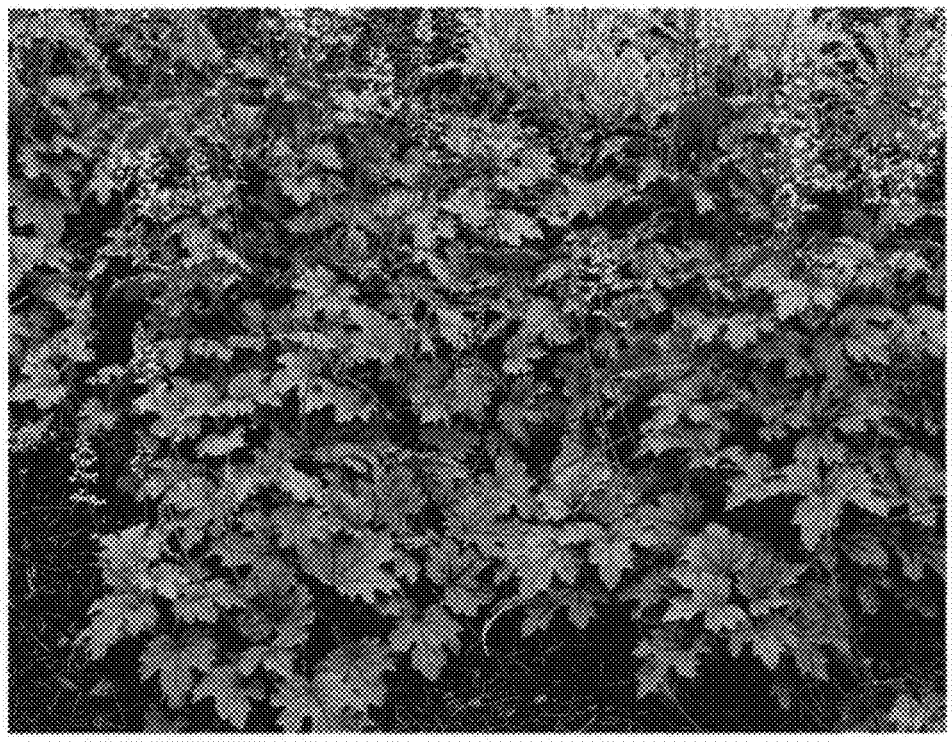

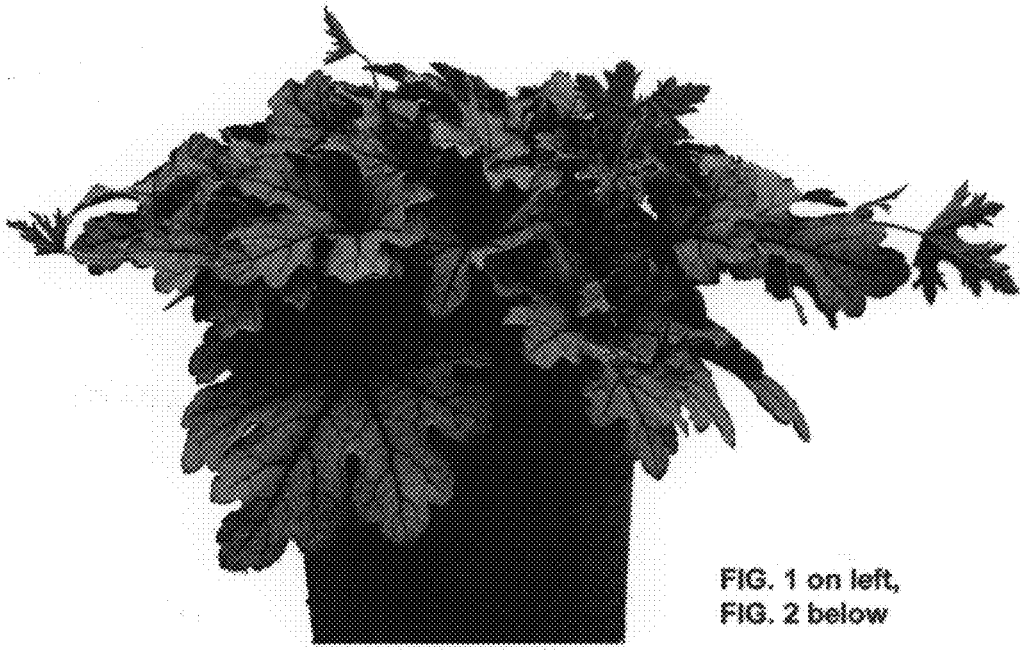
FIG. 1 on left,
FIG. 2 below